(12) United States Patent
Hegazi et al.

(10) Patent No.: US 10,281,401 B2
(45) Date of Patent: May 7, 2019

(54) OPTO-MECHANICAL PART FOR PARABOLIC MIRROR FINE ROTATION AND ON-AXIS LINEAR POSITIONING

(71) Applicant: Saudi Arabian Oil Company, Dhahran OT (SA)

(72) Inventors: Ezzat Hegazi, Ontario (CA); Vincent Cunningham, Ferbane (IE); Christof Brunner, Zurich (CH); Christoph Stamm, Stein am Rhein (CH)

(73) Assignee: Saudi Arabian Oil Company (SA)

( * ) Notice: Subject to any disclaimer, the term of this patent is extended or adjusted under 35 U.S.C. 154(b) by 0 days.

(21) Appl. No.: 15/485,839

(22) Filed: Apr. 12, 2017

(65) Prior Publication Data

US 2017/0299517 A1    Oct. 19, 2017

Related U.S. Application Data

(60) Provisional application No. 62/322,474, filed on Apr. 14, 2016.

(51) Int. Cl.
*G02B 5/10*     (2006.01)
*G02B 7/00*     (2006.01)
(Continued)

(52) U.S. Cl.
CPC ......... *G01N 21/645* (2013.01); *G01N 21/255* (2013.01); *G01N 33/2823* (2013.01);
(Continued)

(58) Field of Classification Search
CPC .............. G01N 21/645; G01N 21/255; G01N 33/2823; G01N 2201/061
See application file for complete search history.

(56) References Cited

U.S. PATENT DOCUMENTS 845,585 A    2/1907   Sharts
3,566,101 A  2/1971   Hagner
(Continued)

FOREIGN PATENT DOCUMENTS

CA    2711801 A1    7/2009
EP    0506063       9/1992
(Continued)

OTHER PUBLICATIONS

Hegazi et al., "Estimation of crude oil grade using time-resolved fluorescence spectra," Talanta, vol. 56, No. 6, Apr. 2002; pp. 989-995.

(Continued)

*Primary Examiner* — David P Porta
*Assistant Examiner* — Djura Malevic
(74) *Attorney, Agent, or Firm* — Fish & Richardson P.C.

(57) ABSTRACT

An opto-mechanical apparatus including a hollow housing member having a first end and a second end, the housing member having a longitudinal axis, a parabolic mirror positioned on a side of to the first end of the housing member, and a mirror adjustment mechanism attached to the second end of the housing member, the mirror adjustment mechanism connected to the parabolic mirror through the housing member, the mirror adjustment mechanism configured to adjust an axial position of the parabolic mirror along the longitudinal axis and to adjust a radial position of the parabolic mirror about the longitudinal axis.

16 Claims, 7 Drawing Sheets

(51) Int. Cl.
  *G01N 21/25* (2006.01)
  *G01N 21/64* (2006.01)
  *G01N 33/28* (2006.01)
  *G02B 7/182* (2006.01)
(52) U.S. Cl.
  CPC .............. *G02B 5/10* (2013.01); *G02B 7/004* (2013.01); *G02B 7/1821* (2013.01); *G02B 7/1825* (2013.01); *G01N 2201/061* (2013.01)

(56) References Cited

U.S. PATENT DOCUMENTS

| | | | |
|---|---|---|---|
| 3,594,083 | A | 7/1971 | Barringer |
| 3,841,769 | A | 10/1974 | Bowerman |
| 3,981,566 | A | 9/1976 | Frank et al. |
| 4,023,891 | A | 6/1977 | Chadwick |
| 4,031,398 | A | 6/1977 | Callis et al. |
| 4,060,314 | A | 11/1977 | Heinz |
| 4,060,315 | A | 11/1977 | Heinz |
| 4,398,798 | A | 8/1983 | Krawczak et al. |
| 4,497,465 | A | 2/1985 | Yeakley et al. |
| 4,651,010 | A | 3/1987 | Javan |
| 4,655,543 | A | 4/1987 | Montagu |
| 4,664,487 | A | 5/1987 | Tam |
| 4,991,815 | A | 2/1991 | Softness |
| 5,283,682 | A | 2/1994 | Ostaszewski |
| 5,422,719 | A | 6/1995 | Goldstein |
| 5,818,582 | A | 10/1998 | Fernandez et al. |
| 6,519,034 | B1 | 2/2003 | Engler et al. |
| 6,525,325 | B1 | 2/2003 | Andrews et al. |
| 6,633,043 | B2 | 10/2003 | Hegazi et al. |
| 7,009,752 | B1 | 3/2006 | Lorell et al. |
| 7,358,498 | B2 * | 4/2008 | Geng ............... G08B 13/19608 250/347 |
| 8,240,941 | B2 | 8/2012 | Kibel |
| 2002/0158211 | A1 | 10/2002 | Gillispie |
| 2003/0133105 | A1 | 7/2003 | Gorelik et al. |
| 2004/0007675 | A1 | 1/2004 | Gillispie et al. |
| 2004/0124366 | A1 | 7/2004 | Zeng et al. |
| 2005/0135874 | A1 | 6/2005 | Baylis et al. |
| 2006/0274811 | A1 | 12/2006 | Tanaka et al. |
| 2008/0173804 | A1 | 7/2008 | Ndo et al. |
| 2008/0298406 | A1 * | 12/2008 | Day ...................... B82Y 20/00 372/39 |
| 2009/0006004 | A1 | 1/2009 | Sens et al. |
| 2011/0303834 | A1 | 12/2011 | Hegazi et al. |
| 2012/0034027 | A1 | 2/2012 | Valois |
| 2012/0057254 | A1 | 3/2012 | Arnone et al. |
| 2014/0198313 | A1 | 7/2014 | Tracey et al. |
| 2015/0009495 | A1 | 1/2015 | Li et al. |
| 2015/0039265 | A1 | 2/2015 | Acharid et al. |
| 2015/0112611 | A1 | 4/2015 | Koseoglu |
| 2015/0168368 | A1 | 6/2015 | Hegazi et al. |
| 2015/0362694 | A1 | 12/2015 | Nguyen et al. |

FOREIGN PATENT DOCUMENTS

| | | |
|---|---|---|
| EP | 0540966 | 5/1993 |
| EP | 1371957 A1 | 12/2003 |
| FR | 2817346 A1 | 5/2002 |
| FR | 2883076 | 9/2006 |
| JP | S60-256108 | 12/1985 |
| JP | H04290933 A | 10/1992 |
| JP | 2010008706 A | 1/2010 |
| JP | 2011106842 A | 6/2011 |

OTHER PUBLICATIONS

Hegazi et al., "New approach for spectral characterization of crude oil using time-resolved fluorescence spectra," Applied Spectroscopy, vol. 55, No. 2, Feb. 2001; pp. 202-207.

Pantoja et al., "Prediction of Crude Oil Properties and Chemical Composition by Means of Steady-State and Time Resolved Fluorescence," Energy Fuels, vol. 25, No. 8, Jul. 2011; pp. 3598-3604.

Ralston et al., "Quantum yields of crude oils," Applied Spectroscopy, vol. 50, No. 12, Dec. 1996; pp. 1563-1568.

Ryder, "Time-resolved fluorescence spectroscopic study of crude petroleum oils: Influence of chemical composition," Applied Spectroscopy, vol. 58, No. 5, May 2004; pp. 613-623.

Ryder et al., "Characterization of crude oils using fluorescence lifetime data," Spectrochimica Acta A, vol. 58, No. 5, Mar. 2002; pp. 1025-1037.

Wang et al., "Fluorescence Lifetime Studies of Crude Oils," Applied Spectroscopy, vol. 48, No. 8, Aug. 1994; pp. 977-984.

International Search Report and Written Opinion issued in International Application No. PCT/US2017/027132 dated Jul. 5, 2017; 12 pages.

Invitation to Pay Additional Fees and Partial International Search Report issued in International Application No. PCT/US2017/027140 dated Jul. 24, 2017; 12 pages.

International Search Report and Written Opinion issued in International Application No. PCT/US2017/027140 dated Sep. 15, 2017; 21 pages.

* cited by examiner

OPTO-MECHANICAL PART FOR PARABOLIC MIRROR FINE ROTATION AND ON-AXIS LINEAR POSITIONING

TECHNICAL FIELD

This specification relates to apparatuses for directing light beams.

BACKGROUND

In many optical setups parabolic mirrors are used to direct a light beam towards a target and to redirect the beam reflected by the target to a detector assembly. To optimize performance, the parabolic mirrors need to be in near-perfect alignment with both the target and the detector assembly. To achieve this positioning, many parabolic mirrors use an adjustable mounting assembly. The mounting assembly has adjusting mechanisms adapted to adjust the parabolic mirrors in both azimuth and elevation. Once the parabolic mirrors are in the proper azimuthal and elevational directions, a locking mechanism in each direction is used to lock the parabolic mirrors in position. The locking mechanisms, however, can act on the adjusting mechanisms, moving the parabolic mirrors out of alignment. Once the parabolic mirrors are out of alignment, the light beam is not aimed directly at the target, which also affects the reflected beam.

SUMMARY

The present specification describes an opto-mechanical apparatus including a hollow housing member having a first end and a second end, the housing member having a longitudinal axis, a parabolic mirror positioned on a side of the first end of the housing member, and a mirror adjustment mechanism connected to the second end of the housing member, the mirror adjustment mechanism connected to the parabolic mirror through the housing member, the mirror adjustment mechanism configured to adjust an axial position of the parabolic mirror along the longitudinal axis, and to adjust a radial position of the parabolic mirror about the longitudinal axis.

The foregoing and other implementations can each, optionally, include one or more of the following features, alone or in combination. In an aspect, the apparatus further including a base plate having a first end and a second end, wherein the first end of the base plate is connected to the first end of the housing member, and wherein the axel passes through the base plate. The apparatus further including a mirror support plate having a first end and a second end, wherein the first end of the mirror support plate is connected to the first end of the axel, and wherein the second end of the mirror support plate is connected to the parabolic mirror. The apparatus further including a hollow retaining ring positioned between the mirror-support plate and the housing member, the retaining ring contacting the return spring on one side of the retaining ring and contacting the mirror adjustment mechanism on the opposite side of the retaining ring, wherein the axel passes through the retaining ring. The apparatus further includes a return spring positioned between the mirror-support plate and the housing member. The mirror adjustment mechanism includes a fine-adjustment screw at least partially screwed into the second end of the housing member, wherein a first end of the fine-adjustment screw protrudes away from the second end of the housing member and a second end of the fine-adjustment screw contacts the retaining ring, wherein the fine-adjustment screw is rotatable to adjust the axial position of the parabolic mirror along the longitudinal axis. The apparatus further including an axel extending through the housing member along the longitudinal axis of the housing member, the axel having a first end and a second end, wherein the first end of the axel is connected to the parabolic mirror.

In a further aspect, the mirror adjustment mechanism includes a drive shaft, wherein the second end of the axel is connected to the drive shaft, a stationary part connected to the second end of the housing member, and a fine-adjustment screw, wherein at least a portion of the fine-adjustment screw is passed through the drive shaft, the fine-adjustment screw having a first end and a second end, wherein the second end abuts the stationary part, wherein the fine-adjustment screw is rotatable to adjust the radial position of the parabolic mirror about the longitudinal axis. The apparatus further including a locking screw configured to be received through a circumferential surface of the housing member connecting the first end and the second end of the housing member, the locking screw configured to lock the parabolic mirror in the axial position and in the radial position.

The present specification also describes a method including generating, by a light source, a light beam, guiding the light beam to an opto-mechanical apparatus including a hollow housing member having a first end and a second end, the housing member having a longitudinal axis, a parabolic mirror connected to the first end of the housing member, and a mirror adjustment mechanism connected to the second end of the housing member, the mirror adjustment mechanism connected to the parabolic mirror through the housing member, the mirror adjustment mechanism configured to adjust an axial position of the parabolic mirror along the longitudinal axis and to adjust a radial position of the parabolic mirror about the longitudinal axis, and adjusting at least one of the axial position or the radial position of the parabolic mirror, using the mirror adjustment mechanism to guide the light beam to irradiate an optical target.

The foregoing and other implementations can each, optionally, include one or more of the following features, alone or in combination. In an aspect, the opto-mechanical apparatus is a first opto-mechanical apparatus, and the method further includes generating a signal in response to irradiating the optical target with the light beam from the light source, guiding the signal to a second opto-mechanical apparatus including: a hollow housing member having a first end and a second end, the housing member having a longitudinal axis, a parabolic mirror connected to the first end of the housing member, and a mirror adjustment mechanism connected to the second end of the housing member, the mirror adjustment mechanism connected to the parabolic mirror through the housing member, the mirror adjustment mechanism configured to adjust an axial position of the parabolic mirror along the longitudinal axis and to adjust a radial position of the parabolic mirror about the longitudinal axis, and adjusting at least one of the axial position or the radial position of the parabolic mirror of the second opto-mechanical apparatus using the mirror adjustment mechanism of the second opto-mechanical apparatus to guide the signal to an optical detector.

In a further aspect, the second opto-mechanical apparatus includes a locking screw configured to be received through a circumferential surface of the housing member of the second opto-mechanical apparatus connecting the first end and the second end of the housing member of the second opto-mechanical apparatus, the locking screw configured to lock the parabolic mirror in the axial position and in the radial position, and wherein the method further includes locking the axial position and the radial position of the parabolic mirror of the second opto-mechanical apparatus using the locking screw of the second opto-mechanical apparatus. The method of claim 10, wherein the signal is a fluorescence signal. The optical target includes refined oil products or crude petroleum oils. The optical target is irradiated with the light beam as the optical target flows through a pipeline. The light source includes a light-emitting diode. The light beam has an intensity in a pico-Joule range and is smaller than 1 nano-Joule. The light beam is a pulsed light beam.

In a further aspect, the first opto-mechanical apparatus includes a locking screw configured to be received through a circumferential surface of the housing member of the first opto-mechanical apparatus connecting the first end and the second end of the housing member of the first opto-mechanical apparatus, the locking screw configured to lock the parabolic mirror in the axial position and in the radial position, and wherein the method further includes locking the axial position and the radial position of the parabolic mirror of the first opto-mechanical apparatus using the locking screw of the first opto-mechanical apparatus. Adjusting the radial position of the parabolic mirror includes adjusting an angle of the parabolic mirror about the longitudinal axis using the mirror adjustment mechanism in increments of about $10^{-3}$ radians.

The details of one or more implementations of the subject matter of this specification are set forth in the accompanying drawings and associated description. Other features, aspects, and advantages of the subject matter will become apparent from the description, the drawings, and the claims.

DETAILED DESCRIPTION

At a high level, this specification generally describes methods and systems, for adjusting a mirror using an opto-mechanical part. In particular, the opto-mechanical part housing a parabolic mirror has been designed and constructed for the purpose of fine rotational and on-axis linear positioning of the parabolic mirror. For rotational positioning, the opto-mechanical part includes a mechanical drive shaft that transmits rotation to an axel, which is connected to the parabolic mirror. For linear positioning, the opto-mechanical part includes a retaining ring and a spring that are connected to the parabolic mirror. Implementation of this configuration provides improved rotational fine adjustment capabilities when compared to direct rotation of the axel. By using a combination of a retaining ring fixed to the axel and a spring loaded mirror support, the on-axis position of the mirror can be adjusted using the same opto-mechanical part.

The opto-mechanical part allows straightforward and convenient access, maneuverability and mirror adjustment within confined spaces, by including the fine adjustment screws for both the rotation and linear positioning of the mirror on the side of the opto-mechanical part with the parabolic mirror on the opposite side. Both the rotational and linear positioning can be locked using a single locking screw. The adjustment of the mirror is done relative to a housing that can be fixed onto the frame of the setup and not relative to the frame itself. In addition, during alignment, the light beam moves in parallel displacements and does not change the angle of propagation, such that it prevents unwanted angular dependent effects. The opto-mechanical part can be applied in optimizing mirror positioning in many different types of optical setups that involve the use of parabolic mirrors, including laser-induced fluorescence setups that require simultaneous alignment of the excitation light beam and the resulting fluorescence emission.

Figure 1A:
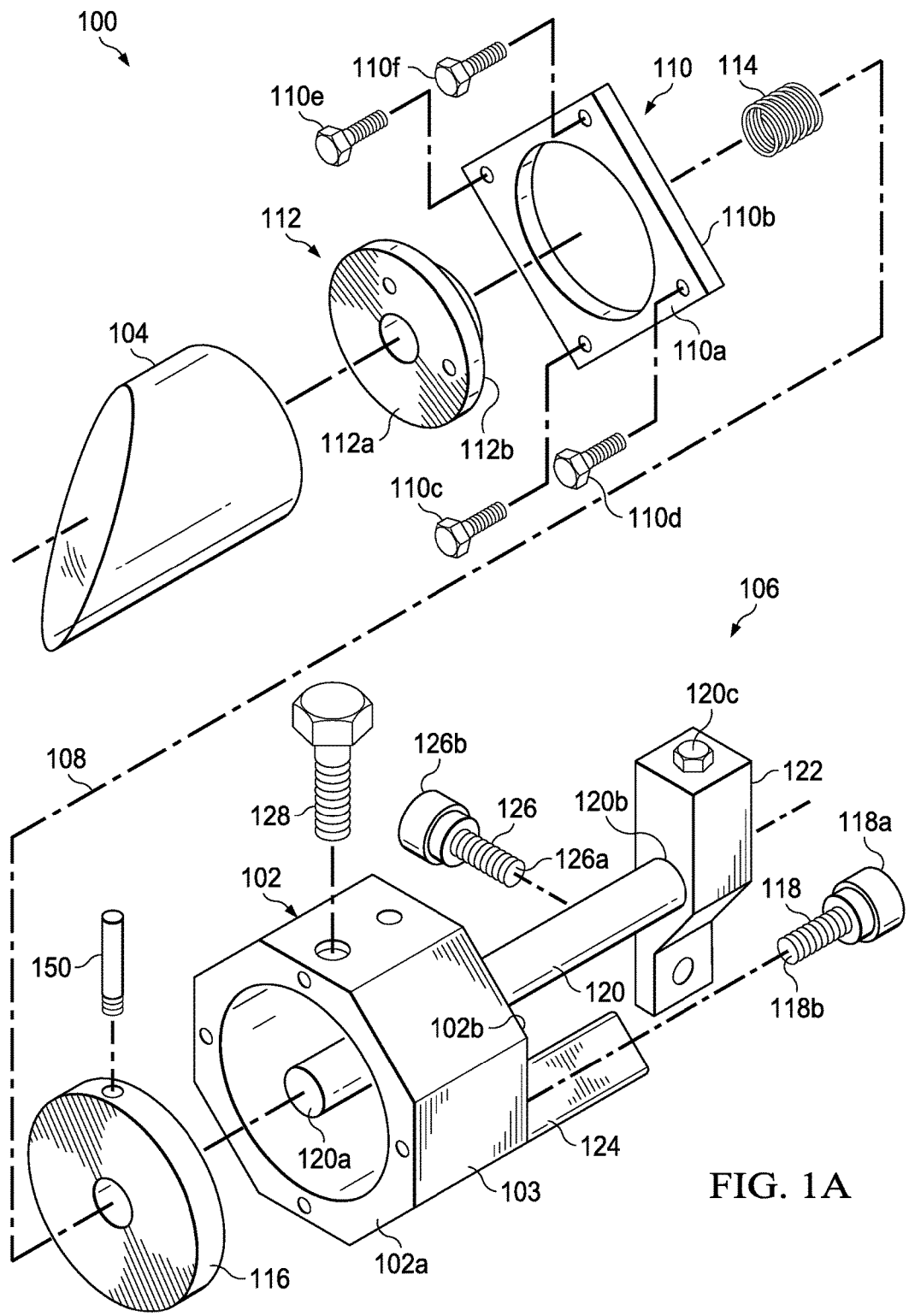
FIG. 1A is an exploded view of an example of an opto-mechanical apparatus.

FIG. 1A is an exploded view of an example of an opto-mechanical apparatus 100. The opto-mechanical apparatus 100 includes an opto-mechanical part 102 and a parabolic mirror 104. The opto-mechanical part 102 includes a hollow housing member 103, a mirror adjustment mechanism 106, a base plate 110, a mirror support plate 112, a return spring 114, a hollow retaining ring 116, a first fine-adjustment screw 118, an axel 120, a drive shaft 122, a stationary part 124, a second fine-adjustment screw 126, and a locking screw 128. The hollow housing member 103 has a first end 102a and a second end 102b. The components of the opto-mechanical apparatus 100 can be assembled to the housing member 103, as described here, along a longitudinal axis 108. The opto-mechanical apparatus 100 includes a parabolic mirror 104 connected to the side of the first end 102a and a mirror adjustment mechanism 106 attached on the side of the second end 102b. The opto-mechanical part 102 includes the base plate 110 positioned between the housing member 103 and the parabolic mirror 104. A first end 110b of the base plate 110 is attached to the first end 102a of the housing member 103. The parabolic mirror 104 resides on the side of the first end 102a of the housing member 103, but is not directly attached to the first end 102a of the housing member 103. The opto-mechanical part 102 includes the mirror support plate 112 positioned between the base plate 110 and the parabolic mirror 104. A first end 112b of the mirror support plate 112 is attached to the second end 110a of the base plate 110. A second end 112a of the mirror support plate 112 is attached to a first end 120a of an axel 120 (described later). The opto-mechanical part 102 includes the return spring 114 positioned between the mirror support plate 112 and the housing member 103. The spring 114 is trapped between the hollow retaining ring 116 and the base plate 110, such that it does not go through the base plate 110, giving a small degree of freedom to move in the longitudinal axis. The axel 120 goes through the hollow retaining ring 116, where the hollow retaining ring 116 is locked to the first end 120a of the axel 120, and also goes through the spring 114 and is attached to the mirror support plate 112 at the first end 120a. The hollow retaining ring 116 is positioned between the mirror support plate 112 and the housing member 103. The inner diameter of the retaining ring 116 is smaller than an inner diameter of the housing member 103. The retaining ring 116 is fitted to the axel 120 and is free to move inside the housing member 103 (for example, rotate freely and move along the axis, only when the locking screw 128 is not holding it in position). The locking screw 128 is open during alignment/positioning of the opto-mechanical apparatus 100. The retaining ring 116 contacts the return spring 114 on one side of the retaining ring 116 and contacts the mirror adjustment mechanism 106 on the opposite side of the retaining ring 116.

The mirror adjustment mechanism 106 includes a first fine-adjustment screw 118. At least a portion of the first screw 118 is screwed into the second end 102b of the housing member 103. A first end 118a of the first screw 118 protrudes away from the second end 102b of the housing member 103. A second end 118b of the first screw 118 contacts the retaining ring 116. The first screw 118 is rotatable to adjust the axial position of the parabolic mirror 104 along the longitudinal axis 118. The base plate 110 is rigidly connected to the housing member 103 by four screws 110c, 110d, 110e, and 110f. The mirror 104 is rigidly connected to the mirror support plate 112, which is rigidly connected to the first end 120a of the axel 120. The hollow retaining ring 116 is fitted to the first end 120a of the axel 120 and is rigidly held by the axel 120. The first screw 118 is a threaded screw that goes through the housing member 103 and makes contact with the hollow retaining ring 116, such that the first screw 118 pushes the hollow retaining ring 116 forward, thereby pushing the mirror 104 forward (because the retaining ring 116 is rigidly connected to the axel 120 and the mirror 104). In response to moving the first screw 118 in the opposite direction (for example, reducing the pressure on the hollow retaining ring 116), the mirror 104 is returned to a neutral position by the elastic force of the compressed spring 114. The axial limits of the position of the mirror 104 are determined by the length of the first screw 118.

The mirror adjustment mechanism 106 also includes the drive shaft 122. The second end 120b of the axel 120 is attached (for example, threadedly or otherwise) to the drive shaft 122. For example, the drive shaft 122 includes a first portion that has a substantially flat surface with an aperture to receive the second end 120b of the axel 120.

The mirror adjustment mechanism 106 additionally includes the stationary part 124 attached to the second end 102b of the housing member 103. The mirror adjustment mechanism 106 further includes the second fine-adjustment screw 126. At least a portion of the second screw 126 is passed through the drive shaft 122. For example, the drive shaft includes a second portion that has a substantially flat surface with an aperture through which the second screw 126 is passed. The second portion of the drive shaft 122 has a thinner cross-section compared to the first portion. The body of the drive shaft 122 tapers from the first portion to the second portion. A length of the first portion of the drive shaft 122 is shorter than a distance between the axel 120 and the stationary part 124. A thickness of the second portion of the drive shaft 122 can be sufficient to pass the second screw 126 allowing an increased radial range of motion for the parabolic mirror 104.

The second screw 126 has a second end 126a which abuts the stationary part 124. The second screw 126 is rotatable, for example, by holding the first end 126b to adjust the radial position of the parabolic mirror 104 about the longitudinal axis 108. The axel 120 passes through the housing member 103. The drive shaft 122 is rigidly connected to the axel 120 through a small screw 120c. The shaft of the second fine-adjustment screw 126 passes through the drive shaft 122. The head of the threaded adjustment screw 126 is sized to prevent passage through the drive shaft 122. The second fine-adjustment screw 126 fits into a threaded hole in the stationary part 124. When the second fine-adjustment screw 126 is screwed (for example, rotated) it pushes the drive shaft 122 (with the head of the second fine-adjustment screw 126), which in-turn rotates the axel 120, thus rotating the mirror 104.

Once the whole assembly is mounted in the desired place (for example with mirror 104 in a neutral position) inside the instrument 504 described with reference to FIG. 5, the radial limits of the mirror 104 are limited by the length of the second fine-adjustment screw 126. The radial range of the mirror 104 is approximately 30 degrees. In some implementations, before mounting the opto-mechanical apparatus 100 in place, the mirror 104 can be rotated manually (coarse alignment) in full 360-degree range by removing the small locking screw 150. The small locking screw 150 is used to rigidly fix the drive shaft 122 to the axel 120.

Figure 1B:
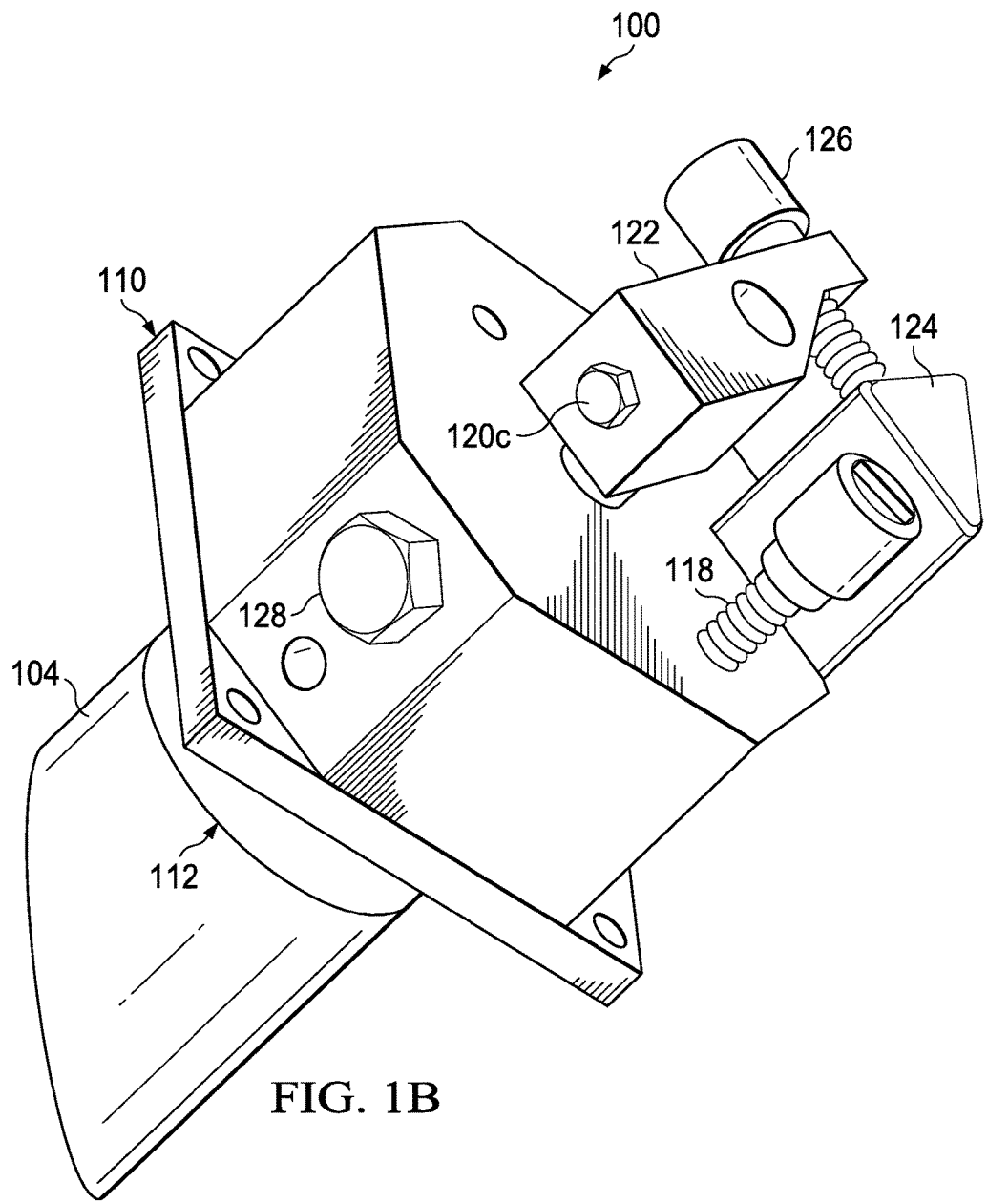
FIG. 1B is an assembled view of an example of an opto-mechanical apparatus.

FIG. 1B is an assembled view of the opto-mechanical apparatus 100. The opto-mechanical part 102 includes a locking screw 128 configured to be received through a circumferential surface of the housing member 103 connecting the first end 102a and the second end 102b of the housing member. The locking screw 128 is configured to lock the parabolic mirror 104 in the axial position and in the radial position. The locking screw 128, when tightened, locks the axel 120 in position. The blockage of the axel 120 jams both screws, 126 and 118. The second fine-adjustment screw 126 is jammed because it acts on the axel 120. The first screw 118 is jammed because it acts on the hollow retaining ring 116, which is attached to the drive shaft 122 by the axel 120. When the first screw 118 moves in and out the whole drive shaft 122 also moves in and out (along the longitudinal axis 108), because it is attached to the hollow retaining ring 116.

That is, using the single locking screw 128, the parabolic mirror 104 can be locked axially and radially on the longitudinal axis. In some implementations, the size of the opto-mechanical part 102 depends on the size of the parabolic mirror 104. For example, for a parabolic mirror with a diameter of 1 inch, the opto-mechanical apparatus 100 can have a size of about 3×2×1 cubic inches.

Figure 1C:
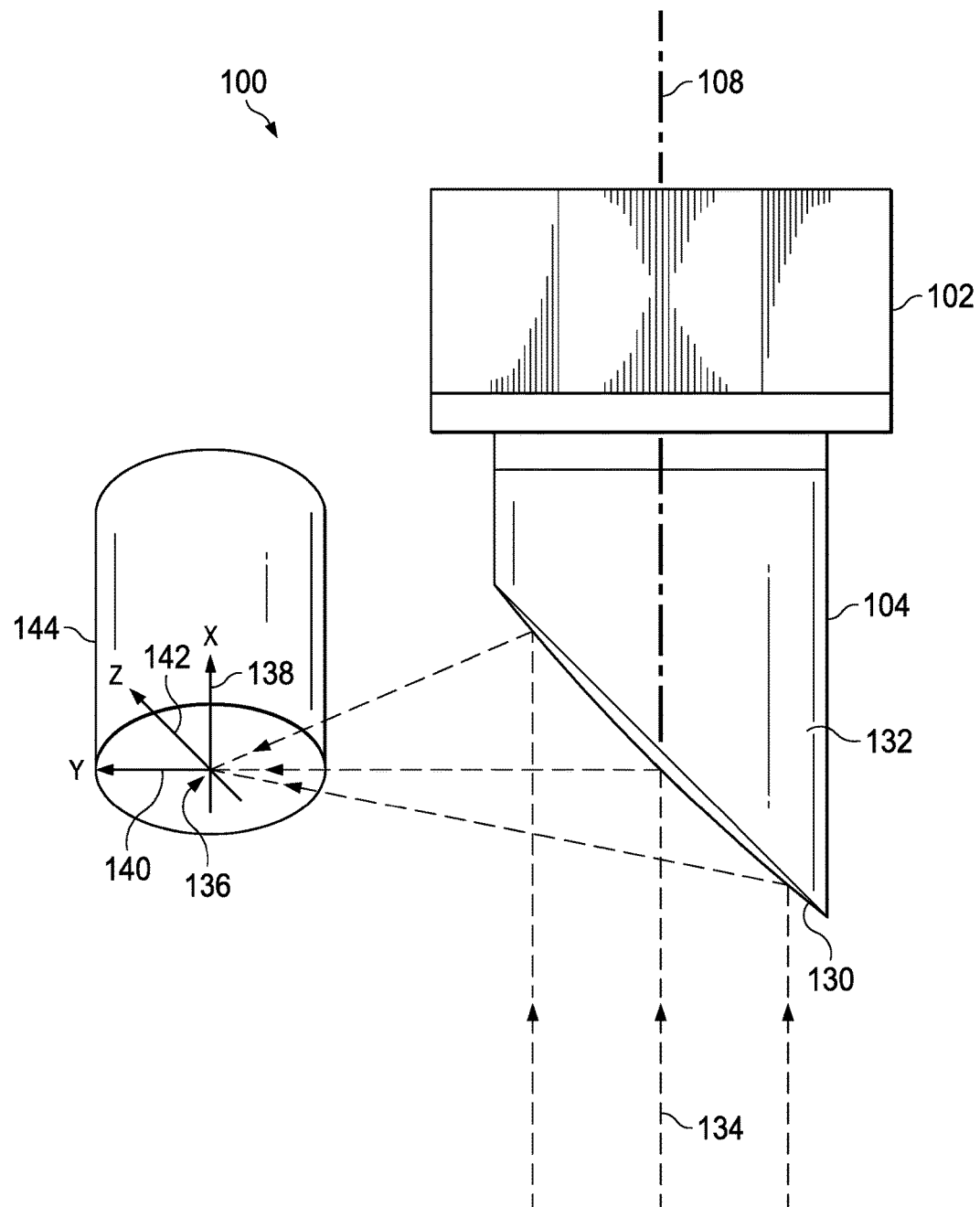
FIG. 1C is a schematic side view of an example of an opto-mechanical apparatus.

FIG. 1C is a schematic diagram of the opto-mechanical apparatus 100 illustrating the connection of the housing member 103 with the parabolic mirror 104. The parabolic mirror 104 includes a mirror surface 130 and a mirror backing 132. The mirror surface 130 is characterized by a parabolic shape, being configured to collect and project a beam of energy 134, such as light, sound, or radio waves into a focal point 136 of the parabolic mirror 104. The mirror backing 132 is attached to the mirror surface 130 and the opto-mechanical part 102. The opto-mechanical part 102 can generate a movement around the axis 108 or along the axis 108 to independently adjust the position of focal point 136 in two directions (along the x-direction 138 or along the y-direction 140). A rotation of the parabolic mirror 104 around the optical axis 108 moves the focal point 136 in the y-direction 140, a movement of the mirror along the optical axis 108 moves the focal point 136 in the x-direction 138. The motion along the z-direction 142 can be inherently achieved from the rotation of the parabolic mirror 104 around the optical axis 108. The plane of all possible focal points 136 can be the surface of a hypothetical cylinder 144. Three-dimensional movement of the focal point 136 can be obtained by illuminating the mirror surface 130 with a collimated beam of energy 134.

Figure 2C:
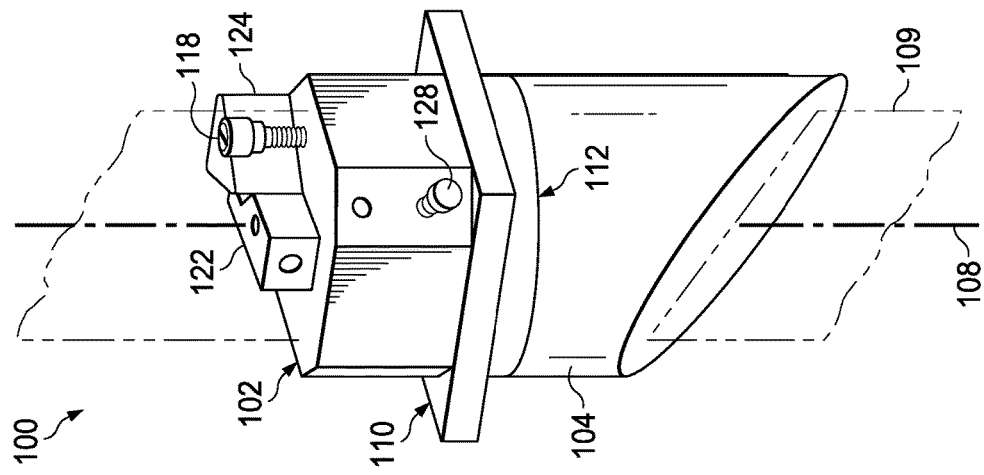
FIGS. 2A-2D illustrate an opto-mechanical apparatus with parabolic mirrors in different radial positions.
Figure 2B:
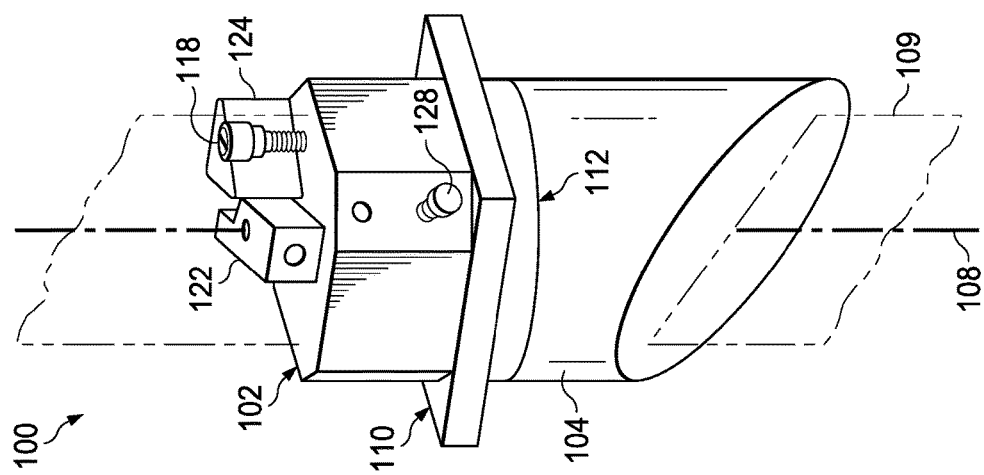
Figure 2A:
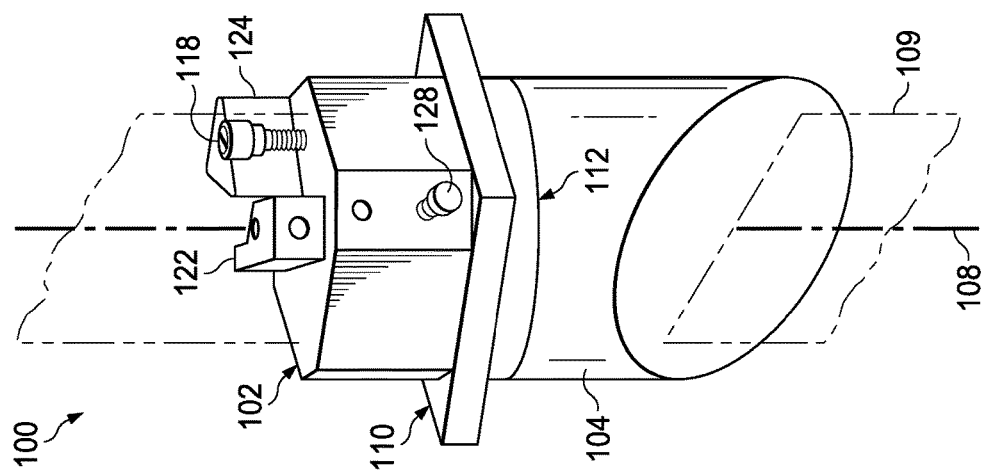

FIGS. 2A-2C illustrate different assembled views of the opto-mechanical apparatus 100 of FIGS. 1A and 1B. The different assembled views of the opto-mechanical apparatus 100 correspond to different positions of the parabolic mirror 104, relative to a vertical plane 109, intersecting the longitudinal axis 108. The rotational motion of the parabolic mirror 104 about the longitudinal axis 108 is effected by rotating the axel 120 that goes through the center of the whole assembly, as described with reference to FIGS. 1A and 1B. In particular, the axel 120 is rotated by turning the second fine-adjustment screw 126 (not shown in FIGS. 2A-2C) into or out of the drive shaft 122. FIGS. 2A-2C illustrate different positions of the parabolic mirror 104 relative to longitudinal axis 108 within a 90° range, however, the parabolic mirror 104 can be rotated to any other angle within a 180° range, using the opto-mechanical apparatus 100.

Figure 2D:
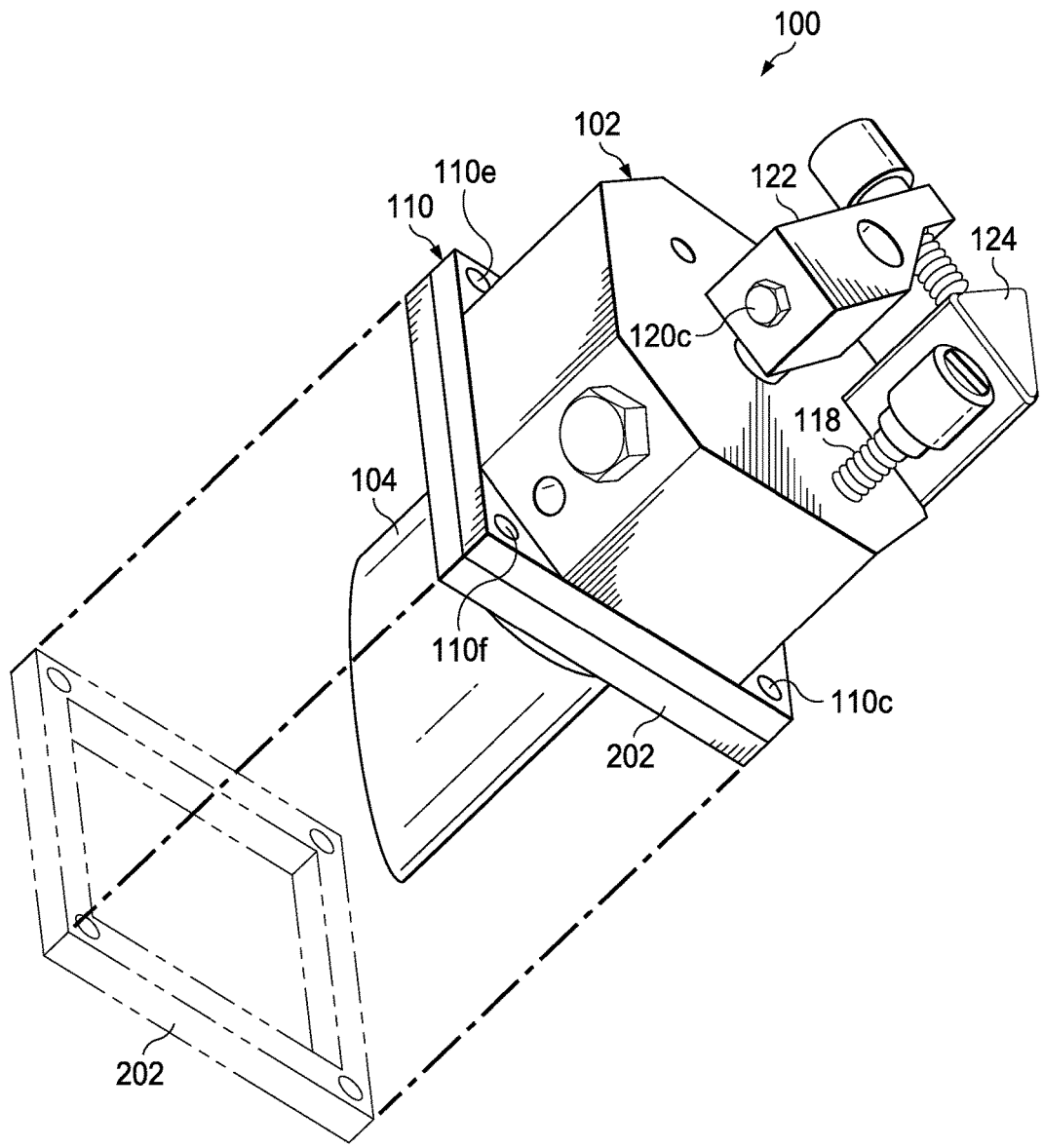

FIG. 2D illustrates an example of an assembled view of the opto-mechanical apparatus 100 of FIGS. 1A and 1B, including a support plate 202. The support plate 202 can be configured to mount the opto-mechanical apparatus 100 using the screws 110c, 110d, 110e, and 110f. The support plate 202 can be part of a panel inside an instrument (such as instrument 504 described with reference to FIG. 5) or it can have a post for use on optical benches. The outer dimensions and geometry of the support plate 202 can be independent from the opto-mechanical apparatus 100. The dimensions and geometry of the opening of the support plate 202 can be dependent on the dimensions of the opto-mechanical apparatus 100. For example, the dimensions and geometry of the opening of the support plate 202 can be selected such that the mirror 104 can pass through the opening.

The opto-mechanical apparatus described with reference to FIGS. 2A-2D can be implemented in any setup that requires a parabolic mirror 104 for the collection and projection of energy, such as light, sound, or radio waves. One example of using the opto-mechanical apparatus 100 with a parabolic mirror 104 is for fluorescence spectroscopy. An implementation of the opto-mechanical apparatus 100 with a parabolic mirror 104 in a fluorescence spectroscopy setup is described with reference to FIG. 3. Other implementations of the opto-mechanical apparatus 100 with a parabolic mirror 104 are also possible.

Figure 3:
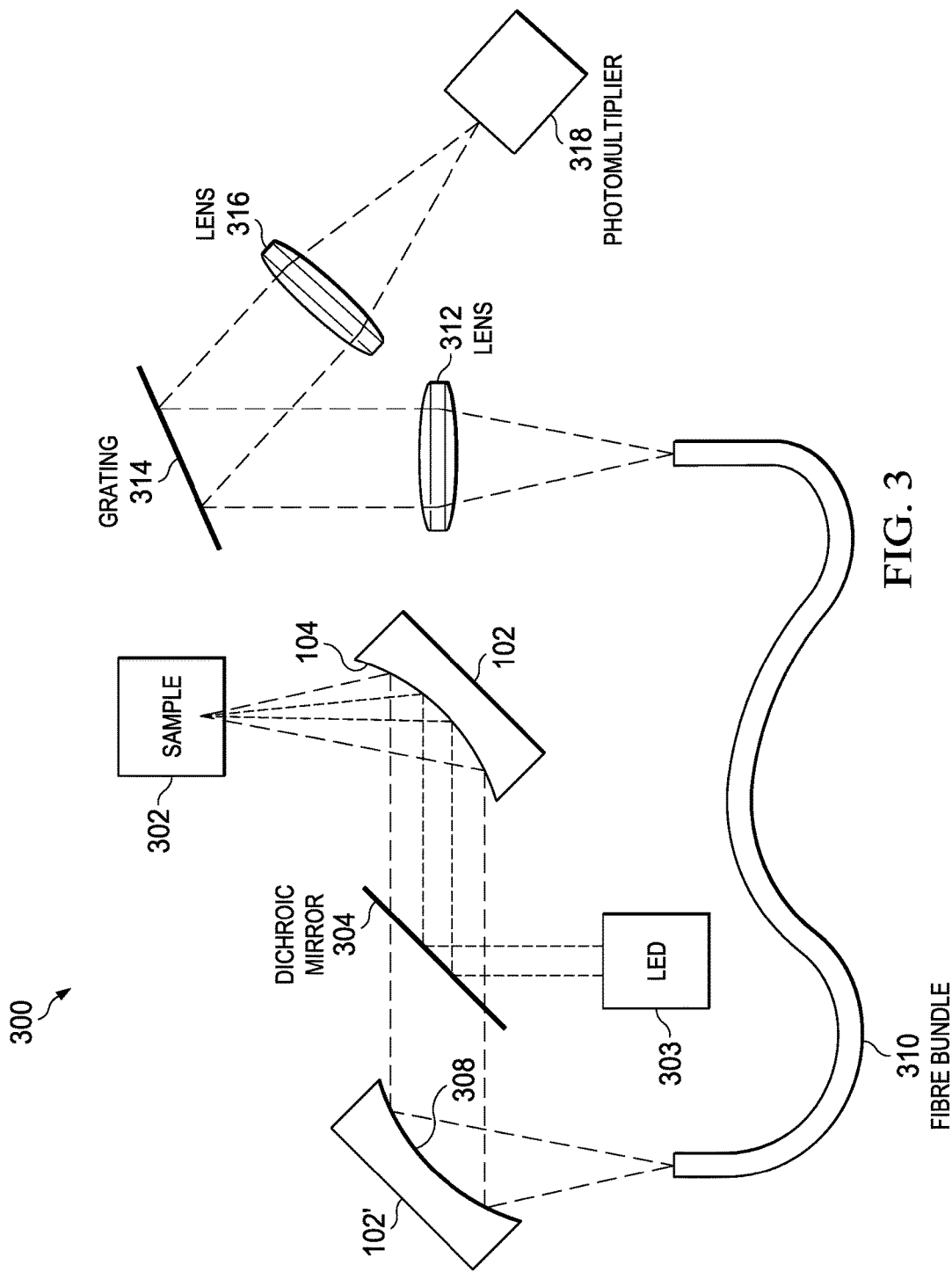
FIG. 3 is a diagrams illustrating examples of a system for adjusting a parabolic mirror position using an opto-mechanical apparatus.

FIG. 3 is a diagram of an example optical setup 300 including the opto-mechanical apparatus 100 described with reference to the earlier figures. The housing member 103 of FIG. 1A can be used to adjust a parabolic mirror 104 to guide a light beam to an optical target 302. The example components of the optical setup 300 can include a light source 303, mirrors 304, 104, and 308, lenses 312 and 316, grating 314, and a detector 318. The light source 303 can be a continuous monochromatic light source that is electronically pulsed or a pulsed light source. The pulsed light source can be a light emitting diode (LED), a pulsed laser having a trigger, such as the fourth harmonic or the third harmonic of a Nd:YAG laser, a pumped pulsed dye laser, or a pumped pulsed MOPO laser, or any other light source.

The light beam 320 can be guided by the mirrors 304 and 104 towards the optical target 302. Mirror 304 can be a dichroic mirror that has significantly different reflection and transmission properties at different wavelengths. The dichroic mirror can selectively pass light beams of a small range of wavelengths while reflecting other wavelengths.

Mirror 104 can be a parabolic mirror configured to direct the light beam 320 towards the optical target (for example, through an optical fiber 510, as described with reference to FIG. 5). The light beam 320 crosses the walls of the container (for example, container 508 in FIG. 5) to irradiate the optical target 302. The optical target 302, irradiated by the step laser beam 107, generates a laser-induced fluorescence signal 322. Mirror 104 can be configured to direct the fluorescent signal 322 towards other components of the optical instrument 104. For example, the fluorescent signal 322 can be filtered by the dichroic mirror 304 and/or an optical filter. The filtered fluorescent signal 322 can be directed by mirror 308 towards an optical fiber bundle 310. Mirror 308 can be a parabolic mirror, for which the position of the focal point is adjusted using an opto-mechanical part 102' that includes the same features and functionality as the opto-mechanical part 102.

The fluorescent signal 322 can be reflected by the mirror 308 towards additional apparatuses for processing the signal. For example, as illustrated in FIG. 3, the mirror 308 can direct the fluorescent signal 322 to an optical fiber bundle 330, which, in turn, can direct the fluorescent signal 322 towards a lens 312. The fluorescent signal 322 can be diverged by the lens 312 on the grating 314 configured to produce diffracted light 324 with different wavelengths dependent upon different grating positions. The diffracted light 324 can be collimated and focused by a lens 316 into a detector 318. If the grating 312 is a fixed diffraction grating, the diffracted light 324 can be projected onto a detector array, such as a CCD, an ICCD, or a PMT. If the grating 312 is a rotating diffraction grating, each wavelength of the diffracted light 324 is projected onto a single detector element.

Figure 4:
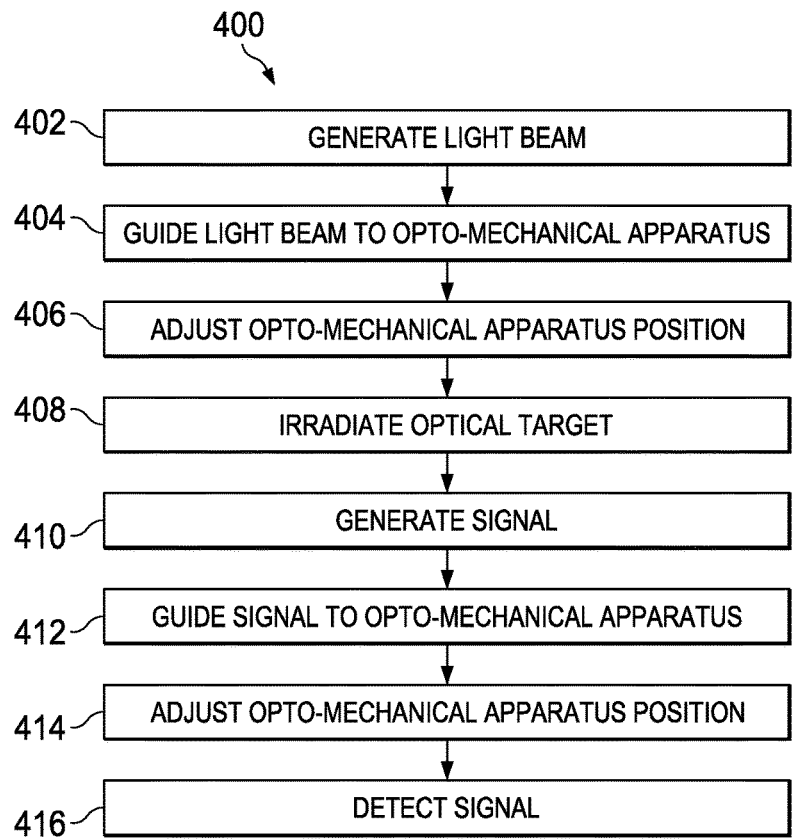
FIG. 4 is a flow chart of an example of a process for adjusting a parabolic mirror according to an implementation of the opto-mechanical part.

FIG. 4 is a flow chart of a method 400 for adjusting a parabolic mirror using an opto-mechanical part, according to an implementation of the apparatus and systems described with reference to the earlier figures. At 402, a light beam is generated by a light source. At 404, the light beam is guided to an opto-mechanical apparatus. The opto-mechanical apparatus can include, for example, the apparatus 100, described with reference to FIGS. 1A and 1B. The source of the light beam can be set up so that the light beam is incident on the parabolic mirror connected to opto-mechanical apparatus at a preferred height and the incidence angle relative to the parabolic mirror. In some implementations, the light source can be set up in a position that is independent from the position of the parabolic mirror and the light beam is directed towards the region of interest of the parabolic mirror, at a preferred incidence angle, through an optical system made of one or more lenses, mirrors, and optical fibers.

At 406, a position of the opto-mechanical apparatus is adjusted. The adjustment can include adjusting at least one of the axial position or the radial position of the parabolic mirror. The adjustment can be performed by using the mirror adjustment mechanism to guide the light beam to irradiate an optical target. The adjustment process can include a coarse adjustment and a fine adjustment. The adjustment process can be initiated after the deactivation of a locking mechanism. The locking mechanism includes manipulation (for example, loosening and tightening) of a locking screw, which is configured to lock the parabolic mirror in the axial position and in the radial position. That is, by loosening the single locking screw, the parabolic mirror can be adjusted axially and radially on the longitudinal axis, within a predetermined range. In some implementations the axial range is about 2 centimeters and the radial range is about 30 degrees. The locking mechanism can prevent an unwanted shift of the mirror 104 during the alignment. The locking screw is perpendicular to the longitudinal axis 108 (the direction of the linear positioning) and also perpendicular to the axial rotation of the drive shaft 122. The mirror 104 is prevented from being shifted out of position since it does not have a degree of freedom along the direction perpendicular to the longitudinal axis 108. The locking screw can freeze the action of the two screws, 126 and 118, simultaneously and instantaneously.

Adjusting the axial position can include rotating a first fine-adjustment screw. For example, the first fine-adjustment screw can be rotated by manipulating an accessible end of the first screw, such as an end that protrudes away from an end of the housing member. The rotation of the first screw applies pressure on a retaining ring, which is transferred to a return-spring. The pressure transferred to the return-spring generates an adjustment of the axial position of the parabolic mirror along the longitudinal axis. The axial increments can depend on the chosen thread pitch of the first fine-adjustment screw. For example, the increments of the position of the first fine-adjustment screw can be about 10 radian degrees (=1/36 of full turn) and the thread pitch can be about 0.3 millimeters to 0.6 millimeters, such that the axial increment can be about 10-20 micrometers.

Adjusting the radial position of the parabolic mirror can include rotating a second screw. For example, the second fine-adjustment screw can be rotated by manipulating an accessible end of the second screw, such as an end that protrudes away from an end of the housing member. The rotation of the second screw applies pressure on a drive-shaft against a stationary part of the main assembly housing. The pressure applied to the drive-shaft is propagated through an axel to the mirror support, such that the rotation of the second screw generates a rotation of the mirror support. In some implementations, the adjustment of the radial position of the parabolic mirror includes adjusting an angle of the parabolic mirror about the longitudinal axis using the mirror adjustment mechanism in angular increments that depend on the chosen thread pitch of the second fine-adjustment screw. For example, the increments of the position of the second fine-adjustment screw can be about 10 radian degrees (=1/36 of full turn) and the thread pitch can be about 0.3 millimeters to 0.6 millimeters. The angular increment is given by the increment of tangential movements or arc length (about 10 to 20 micrometers) divided by the distance of the tangential movement from the center of rotation (about 10 to 20 millimeters), which results in angular increment of about $10^{-3}$ radians. Once the desired axial position and radial position are reached, the locking screw is tightened. The tightening of the locking screw fixes the parabolic mirror in position.

At 408, the light beam irradiates an optical target. At 410, a signal is generated in response to irradiating the optical target with the light beam from the light source. The generated signal can depend on the type of optical target. For example, the signal can be a reflected light beam with the same characteristics as the light beam or a fluorescent signal with the characteristics of the optical target. At 412, the signal is guided to a second opto-mechanical apparatus. At 414, at least one of the axial position or the radial position of the parabolic mirror of the second opto-mechanical apparatus is adjusted to guide the signal towards a detection system. The adjustment process of the second opto-mechanical apparatus can be similar to the adjustment process described with reference to the first opto-mechanical apparatus. The signal can be guided towards the detection system by an optical system including one or more lenses, mirrors, and optical fibers. At 416, the signals are detected and processed.

In some implementations, instead of having two separate adjustment processes, a single adjustment process is performed both for directing the light beam to the optical target and for directing the signal towards the detection system. Steps 402 to 416 can be repeated multiple times to obtain optimal adjustment and generate signals of interest. Output of the method 400 can be provided in a standard tabular format, but other formats are possible and considered to be within the scope of this specification.

Figure 5:
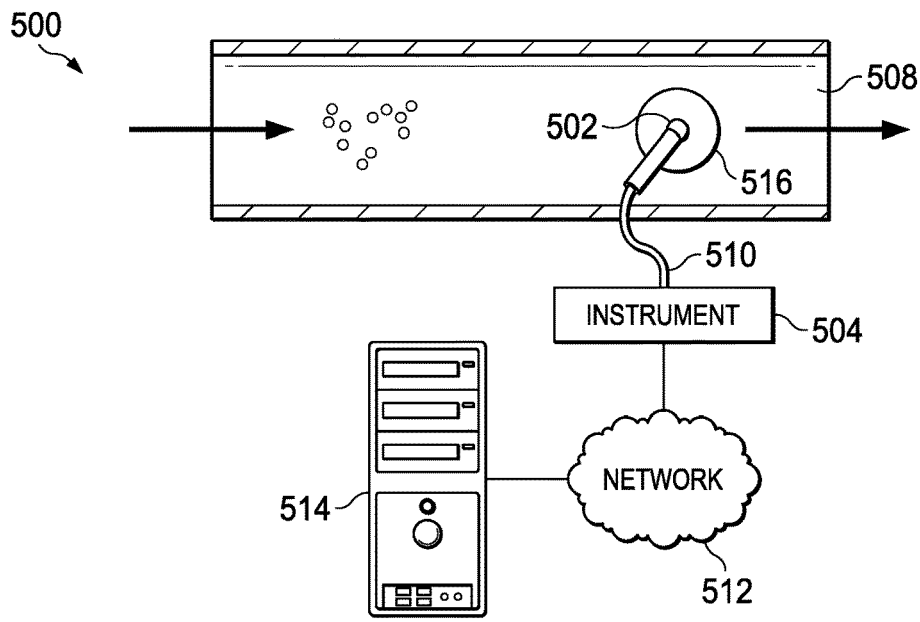
FIG. 5 is a diagram illustrating an example system for adjusting a parabolic mirror according to an implementation of the opto-mechanical part.

FIG. 5 is a diagram illustrating an example of a system 500 provided by the present specification. The system 500 of FIG. 5 is an example of an application of the parabolic mirror adjustment to derive the contour plot of the fluorescence wavelength emission associated to a petroleum oil sample 502. The example components of the system 500 can include an optical instrument 504 including the opto-mechanical apparatus 100 described with reference to FIGS. 1A-1C, a fiber optic bundle 506, a container 508, a network 512, and a computing system 514.

The optical instrument 504 can include a laser source, as described in detail with reference to FIG. 3 and the opto-mechanical apparatus 100, described with reference to FIGS. 1A-1C. In some implementations, the optical instrument 504 can generate a light beam as pulsed electromagnetic waves. The light beam can be guided by the opto-mechanical apparatus 100, described with reference to FIGS. 1A-1C, towards the container 508 by the fiber optic bundle 506. The container 508 can be a pipeline through which a petroleum oil is flowing or a quartz cuvette, in which a petroleum oil sample is stored. The container 508 can include an optical window 516.

The petroleum oil sample 502, irradiated by the light beam, generates a laser-induced fluorescence signal. The fluorescence signal of the petroleum oil sample 502 can be redirected to the optical fiber 506. The optical fiber 506 can transfer the fluorescence signal to the instrument 504 to capture the fluorescence intensity as function of time. In some implementations, an output signal of the instrument 504 can be transmitted over a network 512 to a computing system 514. The computing system 514 can acquire, record and process the fluorescence signal.

Data post processing that can be performed on the fluorescence signal can include, for example, smoothing, reduction of redundant information and correlation algorithms (for example, process 400 described with reference to FIG. 4).

Accordingly, the earlier provided description of example implementations does not define or constrain this specification. Other changes, substitutions, and alterations are also possible without departing from the spirit and scope of this specification.

What is claimed is:

1. An opto-mechanical apparatus comprising:
   a hollow housing member having a first end and a second end, the housing member having a longitudinal axis;
   a parabolic mirror positioned on a side of the first end of the housing member;
   a mirror adjustment mechanism attached to the second end of the housing member, the mirror adjustment mechanism connected to the parabolic mirror through the housing member, the mirror adjustment mechanism configured to adjust an axial position of the parabolic mirror along the longitudinal axis and to adjust a radial position of the parabolic mirror about the longitudinal axis;
   an axle extending through the housing member along the longitudinal axis of the housing member, the axle having a first end and a second end, wherein the first end of the axle is connected to the parabolic mirror;

a mirror support plate having a first end and a second end, wherein the first end of the mirror support plate is attached to the first end of the axle, and wherein the second end of the mirror support plate is attached to the parabolic mirror; and a hollow retaining ring positioned between the mirror support plate and the housing member, the retaining ring contacting a return spring on one side of the retaining ring and contacting the mirror adjustment mechanism on the opposite side of the retaining ring, wherein the axle passes through the retaining ring.

2. The apparatus of claim 1, further comprising:
an axle extending through the housing member along the longitudinal axis of the housing member, the axle having a first end and a second end, wherein the first end of the axle is connected to the parabolic mirror.

3. The apparatus of claim 1, wherein the mirror adjustment mechanism comprises a fine-adjustment screw at least partially screwed into the second end of the housing member, wherein a first end of the fine-adjustment screw protrudes away from the second end of the housing member and a second end of the fine-adjustment screw contacts the retaining ring, wherein the fine-adjustment screw is rotatable to adjust the axial position of the parabolic mirror along the longitudinal axis.

4. The apparatus of claim 1, further comprising a return spring positioned between the mirror support plate and the housing member.

5. The apparatus of claim 4, wherein the mirror adjustment mechanism comprises:
a drive shaft, wherein the second end of the axle is attached to the drive shaft;
a stationary part attached to the second end of the housing member; and
a fine-adjustment screw, wherein at least a portion of the fine-adjustment screw is passed through the drive shaft, the fine-adjustment screw having a first end and a second end, wherein the second end abuts the stationary part, wherein the fine-adjustment screw is rotatable to adjust the radial position of the parabolic mirror about the longitudinal axis.

6. The apparatus of claim 1, further comprising a locking screw configured to be received through a circumferential surface of the housing member connecting the first end and the second end of the housing member, the locking screw configured to lock the parabolic mirror in the axial position and in the radial position.

7. A method comprising:
generating, by a light source, a light beam;
guiding the light beam to a first opto-mechanical apparatus comprising:
a hollow housing member having a first end and a second end, the housing member having a longitudinal axis;
a parabolic mirror attached to the first end of the housing member; and
a mirror adjustment mechanism attached to the second end of the housing member, the mirror adjustment mechanism connected to the parabolic mirror through the housing member, the mirror adjustment mechanism configured to adjust an axial position of the parabolic mirror along the longitudinal axis and to adjust a radial position of the parabolic mirror about the longitudinal axis; and adjusting at least one of the axial position or the radial position of the parabolic mirror using the mirror adjustment mechanism to guide the light beam to irradiate an optical target; and
generating a signal in response to irradiating the optical target with the light beam from the light source;
guiding the signal to a second opto-mechanical apparatus comprising:
a hollow housing member having a first end and a second end, the housing member having a longitudinal axis;
a parabolic mirror attached to the first end of the housing member; and
a mirror adjustment mechanism attached to the second end of the housing member, the mirror adjustment mechanism connected to the parabolic mirror through the housing member, the mirror adjustment mechanism configured to adjust an axial position of the parabolic mirror along the longitudinal axis and to adjust a radial position of the parabolic mirror about the longitudinal axis; and
adjusting at least one of the axial position or the radial position of the parabolic mirror of the second opto-mechanical apparatus using the mirror adjustment mechanism of the second opto-mechanical apparatus to guide the signal to an optical detector.

8. The method of claim 7, wherein the second opto-mechanical apparatus comprises a locking screw configured to be received through a circumferential surface of the housing member of the second opto-mechanical apparatus connecting the first end and the second end of the housing member of the second opto-mechanical apparatus, the locking screw configured to lock the parabolic mirror in the axial position and in the radial position, and wherein the method further comprises locking the axial position and the radial position of the parabolic mirror of the second opto-mechanical apparatus using the locking screw of the second opto-mechanical apparatus.

9. The method of claim 7, wherein the signal is a fluorescence signal.

10. The method of claim 7, wherein the optical target comprises refined oil products or crude petroleum oils.

11. The method of claim 7, wherein the optical target is irradiated with the light beam as the optical target flows through a pipeline.

12. The method of claim 7, wherein the light source comprises a light-emitting diode.

13. The method of claim 7, wherein the light beam has an intensity in a pico-Joule range and is smaller than 1 nano-Joule.

14. The method of claim 7, wherein the first opto-mechanical apparatus comprises a locking screw configured to be received through a circumferential surface of the housing member of the first opto-mechanical apparatus connecting the first end and the second end of the housing member of the first opto-mechanical apparatus, the locking screw configured to lock the parabolic mirror in the axial position and in the radial position, and wherein the method further comprises locking the axial position and the radial position of the parabolic mirror of the first opto-mechanical apparatus using the locking screw of the first opto-mechanical apparatus.

15. The method of claim 7, wherein adjusting the radial position of the parabolic mirror comprises adjusting an angle of the parabolic mirror about the longitudinal axis using the mirror adjustment mechanism in increments of about $10^{-3}$ radians.

16. The method of claim 7, wherein the light beam is a pulsed light beam.

\* \* \* \* \*